United States Patent [19]

Dyer et al.

[11] Patent Number: 4,639,253

[45] Date of Patent: Jan. 27, 1987

[54] NONWOVEN SURGICAL SPONGE WITH X-RAY DETECTABLE ELEMENT

[75] Inventors: John Dyer, Randolph; John W. Kennette, Somerville; Alton H. Bassett, Princeton; Stanley D. Hall, Plainsboro, all of N.J.

[73] Assignee: Johnson & Johnson Products, Inc., New Brunswick, N.J.

[21] Appl. No.: 802,067

[22] Filed: Nov. 25, 1985

Related U.S. Application Data

[63] Continuation of Ser. No. 605,369, Apr. 30, 1984, abandoned.

[51] Int. Cl.4 ............................................. A61F 13/00
[52] U.S. Cl. .................................. 604/362; 428/239
[58] Field of Search ........................ 604/362; 428/239; 128/156

[56] References Cited

U.S. PATENT DOCUMENTS 3,068,547 12/1962 L'Hommedieu ................. 428/239
3,133,538 5/1964 Pratt et al. ........................ 604/362
3,190,289 6/1965 Patience ............................ 604/362
3,566,871 4/1971 Richter ............................. 604/362
3,698,393 10/1972 Stone ................................ 604/362
3,911,922 10/1975 Kliger ............................... 604/362
4,068,666 1/1978 Shiff ................................. 604/362

FOREIGN PATENT DOCUMENTS 2121689 1/1984 United Kingdom ............... 604/362

Primary Examiner—C. Fred Rosenbaum
Assistant Examiner—Karen L. Kaechele
Attorney, Agent, or Firm—Wayne R. Eberhardt

[57] ABSTRACT

A surgical sponge constructed of a nonwoven fabric is provided with an integral X-ray detectable element in the form of a yarn or monofilament which is positioned interiorly of the nonwoven fabric and in the plane thereof. The fabric is produced by placing the X-ray detectable element between two fibrous webs and subjecting the composite material to hydraulic entanglement to produce a patterned, nonwoven fabric.

13 Claims, 6 Drawing Figures

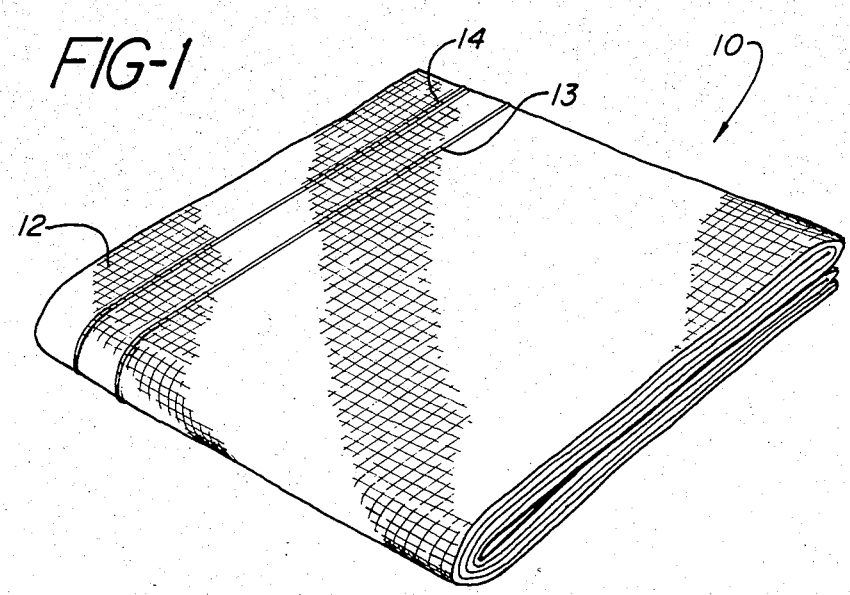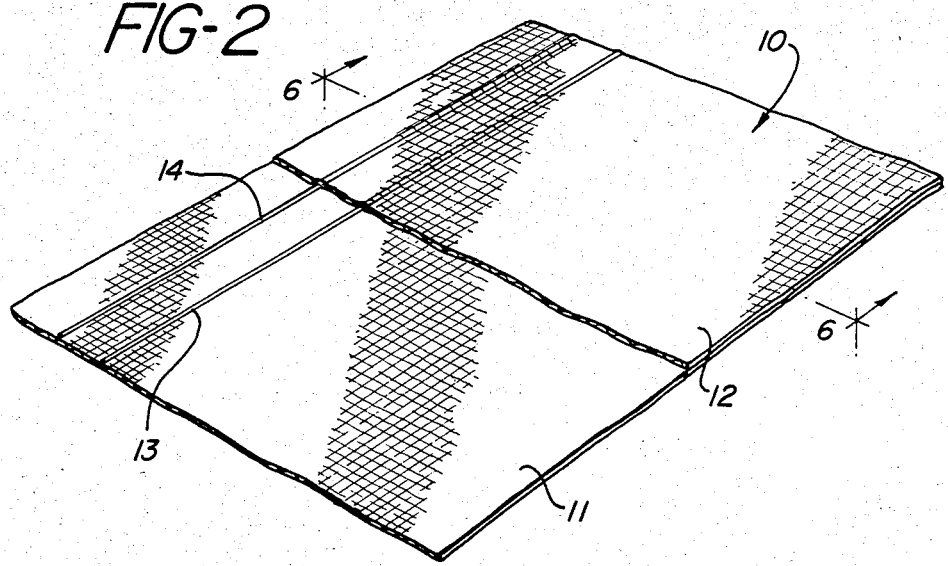

NONWOVEN SURGICAL SPONGE WITH X-RAY DETECTABLE ELEMENT

This application is a continuation of application Ser. No. 605,369, filed Apr. 30, 1984, abandoned.

FIELD OF THE INVENTION

This invention relates to surgical sponges constructed of nonwoven fabric materials, and more particularly, to surgical sponges which include an X-ray detectable element as an integral part of the nonwoven fabric structure.

BACKGROUND OF THE INVENTION

It is common practice in the medical field to include a radiopaque element in surgical sponges so that such sponges can be detected by X-ray if inadvertently left in the body cavity following a surgical procedure. In this context, surgical sponges include folded gauze and nonwoven fabric swabs, woven and knitted laparotomy pads, and cotton balls.

A common X-ray detectable material used in conjunction with surgical sponges is a polymeric filament or ribbon loaded with an X-ray opaque filler material such as barium sulfate. Suitable polymeric materials include polyisobutylene, polyvinyl chloride and copolymers of vinyl acetate and vinyl chloride.

The X-ray detectable elements have been attached to the base sponge material by a variety of techniques. In the case of gauze swabs, a filament has been interwoven into the fabric of the gauze, or attached to the surface of the fabric and folded into the sponge construction. In the case of laparotomy sponges, an X-ray detectable ribbon has been enclosed in a seam stitched along one edge of the pad, and an X-ray detectable filament has been incorporated into the woven handle strap of the pad.

Securing an X-ray detectable element to a nonwoven sponge has presented a problem since nonwovens are produced continuously and at high speed and sewing or stitching the X-ray detectable filament to the nonwoven is not practical from a manufacturing point of view. Some success was had in attaching the X-ray detectable filament to the surface of the nonwoven, usually by heat fusing or resin bonding. Although, this method of attachment was acceptable under manufacturing considerations, the security of attachment was not sufficient to prevent the X-ray detectable element from being pulled off the fabric under some conditions of use.

It is accordingly an object of the present invention to provide a nonwoven surgical sponge with an X-ray detectable element as an integral part of the fabric construction. It is a further object of this invention to provide a method of incorporating an X-ray detectable element into a nonwoven fabric structure without disrupting the fabric or the manufacturing process. These and other objects of the present invention will be apparent from the ensuing description and claims.

SUMMARY

A surgical sponge comprising a nonwoven fabric having an X-ray detectable element as an integral part of the fabric construction is obtained by positioning one or more continuous lengths of the X-ray detectable element between two fibrous webs, and subjecting the composite material to hydraulic entanglement while supported on an apertured belt. The resulting fabric is a nonwoven having the X-ray detectable element positioned interiorly thereof in the plane of the fabric, with the fibers of the fabric intertwined about the element. The X-ray detectable element is preferably a yarn or continuous monofilament and if a monofilament, is preferably hot pressed in a final step to imbed overlying fibers of the nonwoven into the surface of the monofilament.

DESCRIPTION OF DRAWINGS

FIG. 1 is a view in perspective of a folded surgical sponge of the present invention.

FIG. 2 is a partial cross-sectional view in perspective of a single thickness of nonwoven fabric comprising the surgical sponge of FIG. 1.

DESCRIPTION

Figure 3:
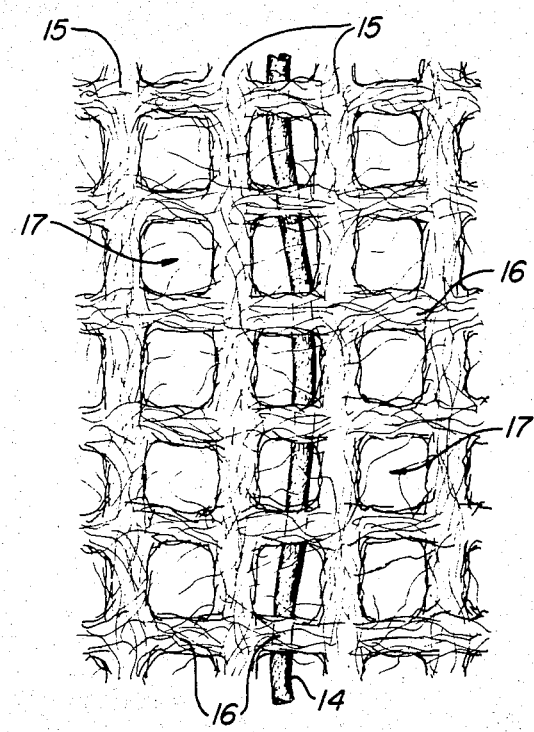
FIG. 3 is an enlarged plan view of a nonwoven fabric including an integral radiopaque monofilament.

The surgical sponges of the present invention are fabricated of nonwoven fabrics manufactured according to conventional hydraulic entanglement methods. In brief, these methods consist of providing a fibrous web of randomly oriented staple length fibers, positioning the web on a patterned, apertured belt, and subjecting the web while supported on the belt to a plurality of high pressure hydraulic jets to entangle the fibers into a pattern conforming to that of the supporting belt. The entangled fibers are thereupon separated from the belt and dried on hot drums to produce a patterned nonwoven fabric. This method of manufacturing is described in detail in U.S. Pat. Nos. 3,068,547; 3,129,466; 3,485,706; 3,494,821; and 3,681,184 and is well known to those skilled in the art.

The nonwoven fabric may comprise any suitable combination of natural and/or synthetic textile materials including cotton, rayon, acrylics, polyester and nylon. A particularly preferred fiber composition is a blend of 70% rayon (1.5 denier, approximately 3 cm staple length) and 30% polyester (1.5 denier, approximately 3 cm staple length). The staple fibers are blended and converted to a fibrous web on conventional textile processing equipment such as a Rando-Webber which produces a web having random fiber orientation.

In the manufacture of t:e nonwoven fabrics of the present invention, two fibrous webs produced from the staple fiber blend are laid one upon the other on a moving belt. At the same time, one or more strands of a radiopaque, X-ray detectable element are positioned between the two webs. The composite material is carried by the belt through the hydraulic entanglement process whereupon the individual webs are unified to form a single thickness of nonwoven fabric with the X-ray detectable element positioned interiorly thereof. The composite nonwoven fabric is thereupon removed from the belt, dried over heated drums, and collected on a roll.

The unified, nonwoven fabric preferably has a total dry weight of from about 1.0 to 3.0 ozs per square yard (30 to 100 g/m$^2$), with the lighter weights limited by the processability of the fibrous webs and the heavier weights limited by the desired utility and construction of the sponge, although higher weights may be preferred for some product applications such as laparotomy pads.

The X-ray detectable material may be any continuous filament, yarn or ribbon of sufficient density to provide an acceptable degree of contrast on a medical X-ray. A suitable monofilament is polyvinylchloride, 0.025 in. in diameter, containing 60% by weight barium sulfate. A suitable yarn is made from a viscose staple containing 40-45% barium sulfate which is spun into a 60 tex singles yarn. Four, six or eight ply yarns are made from the singles yarn for incorporation into the nonwoven fabric.

The X-ray detectable element is preferably dyed or pigmented blue or other suitable color which contrasts sharply with blood. The color permits ready identification of the X-ray detectable element in the sponge, facilitates sponge counting in the operating room and further helps locate the sponge when saturated with blood during use. As a characteristic of the sponges of the present invention, the X-ray detectable element has a lighter covering of nonwoven fibers on the hydraulic jet side of the fabric as compared to the belt side, and is consequently visually more apparent from that side. This increased visibility may be capitalized on when folding the sponge by placing the hydraulic jet side of the fabric to the outside of the sponge.

We have found that the bulkier yarns with lower levels of barium sulfate loading provide less well defined X-ray contrast than the single monofilament material, and the monofilament is accordingly preferred for most applications. An advantage of the yarn however, is that it becomes intimately entangled with the fibrous web materials during the hydraulic entangling process, and thereby forms an integral part of the nonwoven fabric.

The monofilament, while being completely entwined by the fibers of the nonwoven fabric, is not bonded to the fabric, and accordingly can be removed from short lengths of the fabric by pulling from one end. This problem is readily corrected by either heat fusing the thermoplastic monofilament to the entwining fibers of the nonwoven fabric at either end and/or at one or more points between the ends of the fabric, or by heat pressing the monofilament along its length to imbed crossing fibers of the nonwoven fabric into the surface of the monofilament. Heat pressing may be accomplished in connection with the fabric drying step and, since it is performed continuously during production of the nonwoven fabric, does not interfere with the manufacturing process.

The continuous length of nonwoven fabric produced in accordance with the present invention and containing the X-ray detectable element is converted into multi-ply surgical sponges using conventional techniques. Typically, a length fabric is cut and folded to provide a 4×4 inch sponge having 8 or more plys.

The method of the present invention allows the nonwoven fabric to be produced in wide widths with spaced rows of X-ray detectable elements, and then split into narrower widths as required for the sponge with each such narrower width including one or more X-ray detectable elements. In the manufacturing process, one or more X-ray detectable elements are most conveniently positioned between the random, fibrous webs linearly in the machine direction and in a spaced relationship. Alternatively, the elements may be laid between the webs in a sinusoidal, circular, or other pattern as desired. In addition, the X-ray detectable element may be discontinuous if desired provided that each finished sponge product contains a sufficient amount of the element to provide adequate detectability in a medical X-ray.

Referring now to FIG. 1, there is illustrated a surgical sponge according to the present invention comprising a folded, nonwoven fabric 10 which includes integral X-ray detectable elements 13 and 14. In FIG. 2, there is illustrated a single thickness of nonwoven fabric 10 comprising a unified, open patterned, hydraulically entangled fabric. While the two plys of the composite web from which the nonwoven was formed cannot be distinguished in the final product, they are depicted separately in FIG. 2 for purposes of illustration and clarity of understanding. In the manufacturing process, the fibrous web which forms first ply 11 is positioned on the supporting belt, and X-ray detectable filaments 13 and 14 are laid onto the web. The fibrous web which forms second ply 12 is then positioned over ply 11 and the X-ray detectable filaments, and the composite material passed under the hydraulic entanglement jets.

The fibrous webs are crowded, displaced and interspersed into the porous regions of the forming belt by high pressure columnar flow water jets which cause the fiber strands to interlock and provide significant cohesive strength without the addition of a binder. The nonwoven fabric is formed in a negative image of the supporting belt and depending upon the size and spacing of the apertures in the belt, the appearance of the nonwoven fabric may range from a fine, porous continuous sheet to an open, gauze like material. A representative fabric design illustrated in FIG. 3 is a basic square pattern having equally spaced rows of compacted and entangled fibers 15 and 16 in the machine and cross machine directions respectively. Radiopaque monofilament 14 positioned interiorly of the fabric is seen to be enveloped by intertwining fibers of the fabric, particularly where intersecting with the higher density fibers as in the cross-machine direction.

Figure 4:
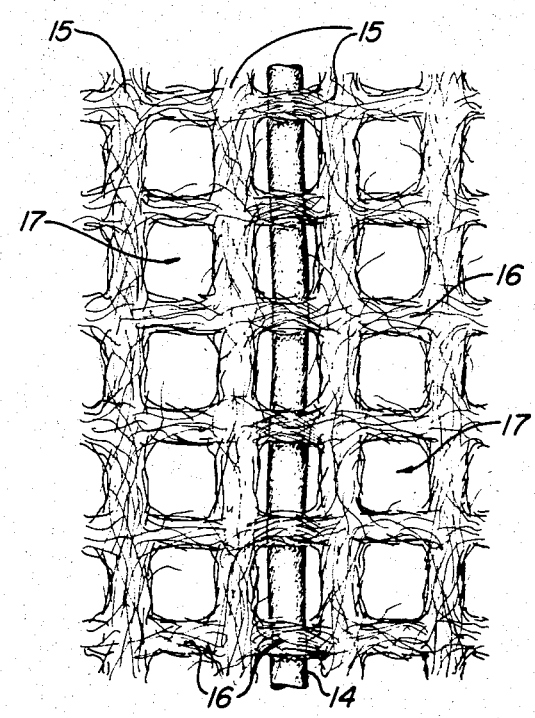
FIG. 4 is a plan view of the fabric of FIG. 2 after hot pressing of the monofilament.

FIG. 4 is another view of the fabric of FIG. 3 after monofilament 14 has been rolled under pressure while in a heated, thermoplastic condition. The monofilament may be rolled immediately as the fabric leaves the drying area of the manufacturing process, or the finished fabric may be passed between heated rolls to compact the monofilament in a separate processing step. The effect of the pressure rolling is to flatten the monofilament somewhat, and to imbed the overlying and underlying fibers of the nonwoven fabric into the surface of the monofilament. The monofilament is thereby secured within the interior of the nonwoven fabric to prevent accidental removal should the end of the filament be caught during use as by grasping with a forceps.

Figure 5:
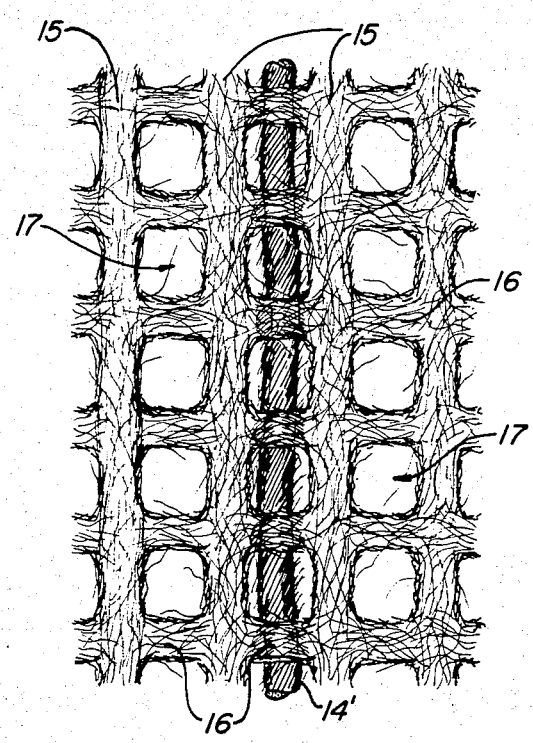
FIG. 5 is an enlarged plan view of a nonwoven fabric with an integral radiopaque yarn.

FIG. 5 illustrates a fabric identical to t:at of FIG. 3 except X-ray detectable element 14 is a twisted yarn of staple length fibers of radiopaque material. As illustrated, the fibers of the nonwoven are entangled with the fibers of the yarn and the yarn is securely held within the interior of the fabric without further processing.

Figure 6:
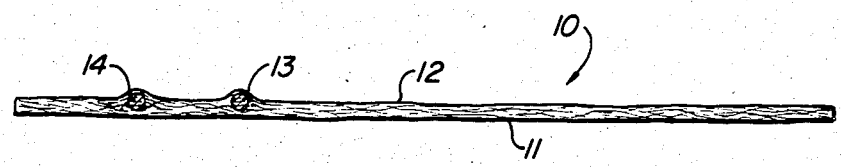
FIG. 6 is a view in cross-section through line 6—6 of FIG. 1.

FIG. 6 illustrates the fabric of FIG. 2 in cross-section through line 6—6 of FIG. 2, and is presented particularly to illustrate that monofilaments 14 and 15 are not centered precisely in the nonwoven fabric, but lie predominantly toward the upper or hydraulic jet side of the fabric. The only consequence of this positioning is greater visibility of the X-ray detectable element on the upper side as compared to the lower side of the fabric.

The nonwoven fabrics of the present invention may be constructed of any suitable fibrous material, and in a variety of patterns, all of which is well within the skill of the art. The fibrous material may, for example, be selected from the group consisting of cotton, rayon, cellulosics, acrylics, polyamides, polyesters, polyolefins, and blends thereof. These and other variations in the surgical sponges as described and illustrated herein will be apparent to those skilled in the art and are included within the scope of the present invention.

We claim:

1. A surgical sponge including an integral X-ray detectable element, said sponge comprising a fibrous, nonwoven fabric consisting essentially of entangled fibers arranged in an interconnecting patterned relationship in the plane of the fabric, and at least one visually colored X-ray detectable element positioned interiorly of said fibrous nonwoven fabric in the plane thereof, the fibers of said nonwoven fabric being intertwined about said X-ray detectable element to provide a fibrous covering of said X-ray detectable element on a first surface of said fabric which is lighter than the fibrous covering on the other surface of said fabric, whereby said X-ray detectable element is more readily visible on said first surface than on said other surface.

2. A sponge of claim 1 wherein said X-ray detectable element is a yarn and the fibers of said nonwoven fabric are intertwined with the fibers of said yarn.

3. A sponge of claim 2 wherein said yarn is a multiply, twisted yarn of viscose fibers containing from 40 to 45 percent barium sulfate.

4. A sponge of claim 1 wherein said X-ray detectable element is a monofilament comprising a thermoplastic polymeric material containing about 60% barium sulfate.

5. A sponge of claim 4 wherein said thermoplastic polymeric material is selected from the group consisting of polyisobutylene, polyvinyl chloride, and copolymers of vinyl acetate and vinyl chloride.

6. A sponge of claim 5 wherein the nonwoven fibers crossing over and under said monofilament are imbedded into the surface of said monofilament.

7. A sponge of claim 1 wherein said nonwoven fabric comprises fibrous material selected from the group consisting of cotton, rayon, cellulosics, acrylics, polyamides, polyesters, polyolefins, and blends thereof.

8. A sponge of claim 7 wherein said nonwoven fabric comprises a blend of about 70% by weight rayon and 30% by weight polyester staple fibers.

9. A sponge of claim 8 wherein said nonwoven fabric has a weight of from about 30 to 100 $g/m^2$.

10. A sponge of claim 1 wherein the arrangement of said entangled fibers define a substantially rectangular pattern in said nonwoven fabric having from about 8 to 25 openings per inch in both machine and cross-machine directions.

11. A folded, surgical sponge including an integral X-ray detectable element, said sponge comprising a fibrous, nonwoven fabric consisting essentially of entangled fibers arranged in an interconnecting patterned relationship in the plane of the fabric, and at least one visually colored X-ray detectable element positioned interiorly of said fibrous nonwoven fabric in the plane thereof, the fibers of said nonwoven fabric being intertwined about said X-ray detectable element to provide a fibrous covering of said X-ray detectable element on a first surface of said fabric which is lighter than the fibrous covering on the other surface of said fabric, whereby said X-ray detectable element is more readily visible on said first surface than on said other surface, said fabric being folded to place said first surface to the outside of said sponge.

12. A sponge of claim 11 wherein said X-ray detectable element is a yarn or monofilament.

13. A sponge of claim 11 wherein said X-ray detectable element is colored to contrast with blood.

* * * * *